US011224605B2

(12) United States Patent
Vigsnæs et al.

(10) Patent No.: US 11,224,605 B2
(45) Date of Patent: *Jan. 18, 2022

(54) SYNTHETIC COMPOSITION

(71) Applicant: Glycom A/S, Hørsholm (DK)

(72) Inventors: Louise Kristine Vigsnæs, Copenhagen (DK); Bruce McConnell, La Tour de Peilz (CH); Emma Elison, Malmö (SE)

(73) Assignee: Glycom A/S, Hørsholm (DK)

( * ) Notice: Subject to any disclaimer, the term of this patent is extended or adjusted under 35 U.S.C. 154(b) by 205 days.

This patent is subject to a terminal disclaimer.

(21) Appl. No.: 16/303,131

(22) PCT Filed: May 19, 2017

(86) PCT No.: PCT/DK2017/050165
§ 371 (c)(1),
(2) Date: Nov. 19, 2018

(87) PCT Pub. No.: WO2017/198276
PCT Pub. Date: Nov. 23, 2017

(65) Prior Publication Data
US 2020/0330492 A1    Oct. 22, 2020

(51) Int. Cl.
*A61K 31/702* (2006.01)
*A61P 1/00* (2006.01)
*A61P 25/00* (2006.01)

(52) U.S. Cl.
CPC .............. *A61K 31/702* (2013.01); *A61P 1/00* (2018.01); *A61P 25/00* (2018.01)

(58) Field of Classification Search
CPC ........... A61K 31/702; A61P 1/00; A61P 25/00
See application file for complete search history.

(56) References Cited

U.S. PATENT DOCUMENTS

| 10,828,313 | B2 * | 11/2020 | Salomonsson | A61P 3/00 |
| 10,881,674 | B2 * | 1/2021 | McConnell | A61K 31/702 |
| 10,987,368 | B2 * | 4/2021 | Vigsnæs et al. | A23L 33/21 |
| 2012/0171166 | A1 * | 7/2012 | Chow | A61K 31/702 424/93.4 |
| 2012/0172319 | A1 | 7/2012 | Chow et al. | |
| 2012/0294840 | A1 * | 11/2012 | Newburg | A61P 1/00 424/93.44 |
| 2015/0305384 | A1 | 10/2015 | Chichlowski et al. | |

FOREIGN PATENT DOCUMENTS

| WO | 01/04341 A1 | 1/2001 |
| WO | 2007101862 A1 | 9/2007 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012007588 A9 | 1/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013054001 A1 | 4/2013 |
| WO | 2013091660 A1 | 6/2013 |
| WO | 2013139344 A1 | 9/2013 |
| WO | 2013154725 A1 | 10/2013 |
| WO | 2014100022 A1 | 6/2014 |
| WO | 2015157098 A1 | 10/2015 |
| WO | 2016066175 A1 | 5/2016 |
| WO | 2017/071715 A1 | 5/2017 |
| WO | 2017/071716 A1 | 5/2017 |

OTHER PUBLICATIONS

Spiller (Neuropharmacology; 55 (2008) 1072-1080).*
PCT/DK2017/050165, Notification of Transmittal of the International Search Report and the Written Opinion of the International Searching Authority, or the Declaration. dated Aug. 3, 2017, pp. 1-10.
T.A. Jenkins et al., "Influence of Tryptophan and Serotonin on Mood and Cognition with a Possible Role of the Gut-Brain Axis", Nutrients 2016, 8, 56; doi:10.3390/nu8010056, Jan. 20, 2016, pp. 1-15.
EPO, Supplementary European Search Report, EP17798803, dated Sep. 12, 2019, pp. 1-6.
A.J. Tarr, "The prebiotics 3' Sialyllactose and 6' Sialyllactose diminish stressor-induced anziety-like behavior and colonic microbiota alterations: evidence for effects on the gut-brain axis", HHS Public Access, Brain Behav Immun, Nov. 2015, pp. 1-30.
Feng-Yan Yu et al., "Comparison of 5-hydroxytryptophan signaling pathway characteristics in diarrhea-predominant irritable bowel syndrome and ulcerative colitis", World Journal of Gastroenterology, Mar. 28, 2016, pp. 3451-3459.
Shen-Hao Wang et al., "Decreased expression of serotonin in the jejunum and increased numbers of mast cells in the terminal ileum in patients with irritable bowel syndrome", World Journal of Gastroenterology, Dec. 7, 2007, pp. 6041-6047.
Mahalia Mcgill et al., "Disruption of Serotonin Signaling Results in Loss of Coordinated Tone Development and Subsequent Inhibition of Peristalsis in Guinea pig Distal Colon", GASEB Journal vol. 30, No. 1 supplement, Apr. 1, 2016, pp. 1-2.
Anna Klindworth et al., "Evaluation of general 16S ribosomal RNA gene PCR primers for classical and next-generation sequencing-based diversity studies", Nucleic Acids Research, 2013, vol. 41, No. 1, Aug. 28, 2012, pp. 1-11.
Sandra JM Ten Bruggecate et al., "Functional role and mechanisms of sialyllactose and other sialylated milk oligosaccharides", Nutrition Reviews® vol. 72(6):, May 14, 2014, pp. 377-389.
Siliva Rudloff et al., "Incorporation of orally applied 13C-galactose into milk lactose and oligosaccharides", Glycobiology vol. 16 No. 6, Feb. 22, 2006, pp. 477-487.

(Continued)

*Primary Examiner* — Pancham Bakshi
(74) *Attorney, Agent, or Firm* — Kunzler Bean & Adamson

(57) ABSTRACT

The application relates to synthetic compositions containing one or more human milk oligosaccharides for treating serotonin and/or tryptophan dysregulation.

13 Claims, No Drawings

(56) References Cited

OTHER PUBLICATIONS

Eugenia Bezirtzoglou et al., "Microbiota profile in feces of breast- and formula-fed newborns by using fluorescence in situ hybridization (FISH)", Anaerobe vol. 17, Apr. 8, 2011, pp. 478-482.

Tadasu Urashima et al., "Milk Oligosaccharides", Urashima Book, 2011, pp. 1-99.

Orazio Gabrielli et al., "Preterm Milk Oligosaccharides During the First Month of Lactation", Pediatrics vol. 128, No. 6, Nov. 28, 2011, pp. e1520-e1531.

C. Faure et al., "Serotonin signalling is altered in irritable bowel syndrome with diarrhea but not in functional dyspepsia in pediatric age patients", Gastroenterology, NIH Public Access Author Manuscript, Jul. 2010, pp. 1-20.

P. Fitzgearld et al., "Tryptophan catabolism in females with irritable bowel syndrome: relationship to interferon-gamma, severity of symptoms and psychiatric co-morbidity", Neurogastroenterol Motil (2008) 20, Jul. 6, 2008, pp. 1291-1297.

Glenn R. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2107, pp. 491-502, 2017.

Monique Haarman et al., "Quantitative Real-Time PCR Assays To Identify and Quantify Fecal *Bifidobacterium* Species in Infants Receiving a Prebiotic Infant Formula", Applied and Environmental Microbiology, vol. 71, No. 5, May 2005, p. 2318-2324.

\* cited by examiner

SYNTHETIC COMPOSITION

FIELD OF THE INVENTION

This invention relates to a method and composition for improving gastrointestinal motility, secretion and sensation by regulating serotonin synthesis in humans.

BACKGROUND OF THE INVENTION

A regulated communication between the gut and the brain plays a very important role in the wellbeing of a human, and normal gastrointestinal (GI) health relies on a properly functioning brain-gut axis. Serotonin, which functions as a neurotransmitter, facilitates communication between the enteric nervous system and the rest of the gut, and plays an important role in regulation of gut motility and secretion. Serotonin can activate neurons causing either bowel contraction or relaxation, can initiate secretion, and contribute to the dilution and neutralization of luminal contents, causing protective responses to eliminate luminal pathogens.

The GI tract is the largest producer of serotonin in the human body. Since 95 percent of the serotonin is found in the gut, an imbalance in its signalling can cause alterations in motility and secretion. This has been shown in a study, where disruption of serotonin signalling resulted in loss of peristaltic motility (McGill et al. *FASEB J.* 30, Supplement 1254.6 (2016)).

Tryptophan is the precursor of a wide array of metabolites, which are involved in a variety of aspects of human nutrition and metabolism. Tryptophan can be metabolized to serotonin, however, it can also enter the kynurenine pathway. The kynurenine pathway is regulated by pro-inflammatory cytokines such as IFN-γ and TNF-α, and metabolites from this pathway have been shown to be able to negatively modulate immune responses. Hence, accumulating evidence indicates that shunting tryptophan down the kynurenine pathway at the expenses of serotonin biosynthesis may cause abnormalities in serotonin signalling and could lead to functional GI disorders such as irritable bowel syndrome (IBS), celiac disease and inflammatory bowel disease (IBD). Studies have shown that IBS patients have impaired levels of serotonin compared to controls, with higher levels in IBS-D and lower levels in IBS-C (Yu et al. *World J. Gastroenterol.* 22, 3451 (2016); Wang et al. ibid. 13, 6041 (2007)). Additionally, abnormal tryptophan catabolism has been found to correlate with severe IBS symptoms (Faure et al. *Gastroenterology* 139, 249 (2010); Fitzgerald et al. *Neurogastroenterol. Motil.* 20, 1291 (2008)). Since tryptophan is an essential amino acid with an estimated dietary requirement of 5 mg/kg/day and it is the limiting amino acid in nearly all protein sources, dietary sources of tryptophan may not be enough to obtain a regulated serotonin synthesis, and maintain normal GI function. Therefore, there is a need for a safe, effective intervention for obtaining sufficient tryptophan for regulating serotonin synthesis.

In addition to tryptophan and serotonin metabolism, an optimal functioning GI tract requires a healthy bacterial population of beneficial bacteria. The human intestinal microbiota is a complex and very dynamic microbial ecosystem that consists of various populations, which are important to preserve human health. Selective stimulation of specific beneficial intestinal bacteria to promote their growth and metabolic activity could be a helpful approach in regulating the tryptophan and serotonin metabolic pathways, resulting in improvement of gut motility and secretion.

Human milk oligosaccharides (HMOs) are a heterogeneous mixture of soluble glycans found in human milk. They are the third most abundant solid component after lactose and lipids in human milk and are present in concentrations of 5-25 g/l (Gabrielli et al. Pediatrics 128, e1520 (2011)). HMOs are resistant to enzymatic hydrolysis in the small intestine and are thus largely undigested and unabsorbed (ten Bruggencate et al. *Nutrition Reviews* 72, 377 (2014); Rudloff et al. *Glycobiology* 16, 477 (2006)). The majority of HMOs that reaches the colon serves as a substrate to shape the gut ecosystem by selectively stimulating the growth of specific beneficial bacteria. HMOs are believed to substantially modulate the infant gut microbiota and play a decisive role in the differences in the microbiota of formula-fed and breast-fed infants. These differences include the predominance of *Bifidobacterium* in the gut of breast-fed infants compared to a more diverse gut microbiota in formula-fed infants (Bezirtzoglou et al. *Anaerobe* 17, 478 (2011)). This is viewed as beneficial for the infant because strains of *Bifidobacterium* species and their metabolites are believed to have a positive effect on human health (Rudloff et al. *Glycobiology* 16, 477 (2006); Bezirtzoglou et al. *Anaerobe* 17, 478 (2011)). Recently, it has also been demonstrated that some sialylated and fucosylated HMOs has a positive effect on the growth of certain strains of *Bifidobacterium* species that are typically found in both infant and adult microbiota (WO 2013/154725).

WO 2013/054001 has recently described a positive correlation between the level of serotonin in the blood and proportion of bifidobacteria and/or clostridia species in the intestine flora of tested individuals.

However, the effect of HMOs on serotonin level and gut motility has never been studied and therefore is unknown. Therefore, there remains a need for a safe, well tolerated and effective way of managing serotonin synthesis and thereby improve gut motility.

SUMMARY OF THE INVENTION

The present invention provides synthetic compositions comprising one or more human milk oligosaccharides (HMOs) that can be advantageously used for regulating serotonin synthesis, and improving gut motility and secretion, in a human individual.

Accordingly,
  a first aspect of this invention relates to one or more human milk oligosaccharides for use in the prophylaxis or treatment of a symptom or disease associated with serotonin and/or tryptophan dysregulation in a human;
  a second aspect of this invention relates to one or more human milk oligosaccharides for use in the prophylaxis or treatment of serotonin and/or tryptophan dysregulation in a human, in particular in an irritable bowel symptom (IBS) patient;
  a third aspect of this invention relates to one or more human milk oligosaccharides for use in improving physiological and/or psychological conditions associated with serotonin and/or tryptophan dysregulation in a human;
  a fourth aspect of this invention relates to a synthetic composition for use in the prophylaxis or treatment of a symptom or disease associated with serotonin and/or tryptophan dysregulation in a human, the composition comprising an effective amount of one or more human milk oligosaccharides;
  a fifth aspect of this invention relates to a synthetic composition for use in the prophylaxis or treatment of serotonin and/or tryptophan dysregulation in a human, in particular in an irritable bowel symptom (IBS) patient, the composition comprising an effective amount of one or more human milk oligosaccharides;

a sixth aspect of this invention relates to a synthetic composition for use in improving physiological and/or psychological conditions associated with serotonin and/or tryptophan dysregulation in a human, the composition comprising an effective amount of one or more human milk oligosaccharides;

a seventh aspect of this invention provides a method for the prophylaxis or treatment of a symptom or disease associated with serotonin and/or tryptophan dysregulation in a human, the method comprising administering to the human an effective amount of one or more human milk oligosaccharides;

an eighth aspect of this invention provides a method for the prophylaxis or treatment of serotonin and/or tryptophan dysregulation in a human, the method comprising administering to the human an efficient amount of one or more human milk oligosaccharides;

a ninth aspect of this invention provides a method for improving physiological and/or psychological conditions associated with serotonin and/or tryptophan dysregulation in a human, the composition comprising an effective amount of one or more human milk oligosaccharides.

Preferably, the human milk oligosaccharide is 2'-FL, 3-FL, DFL, 3'-SL, 6'-SL, LNnT, LNT or LNFP-I or a mixture thereof. For example, the composition can comprise a mixture of a fucosylated HMO such as 2'-FL and/or DFL and a non-fucosylated neutral HMO such as LNnT or LNT, or both. In one preferred embodiment, the human milk oligosaccharide is a mixture of 2'-FL and LNnT and/or LNT. In this embodiment, the 2'-FL and LNnT/LNT may be present in a mass ratio of about 5:1 to 1:1; more preferably about 4:1 to 2:1. In another preferred embodiment, the human milk oligosaccharide is a mix of 2'-FL and/or DFL and LNnT and/or LNT. In this embodiment, the 2'-FL/DFL and LNnT/LNT may be present in a mass ratio of about 5:1 to 1:1; more preferably about 4:1 to 2:1.

Preferably, the amount of HMOs is effective to increase the abundance of bifidobacteria in the gastrointestinal tract and improve gut motility of the concerned human in need. For example, the amount may be about 1 g to about 15 g per day; for example about 3 g to about 10 g per day. More preferably an amount of about 3 g to about 7 g is administered per day.

In an embodiment, the synthetic composition can be a nutritional or pharmaceutical composition. Preferably, synthetic composition of the invention is administered daily. Furthermore, the synthetic composition of the invention is preferably administered for a period of at least one month, such as at least 2 months or for a longer period of time, for example chronically on an ongoing basis.

Synthetic composition of the invention may be administered to the human or patient as a daily dose of about 1 g to about 15 g, such as from about 3 g to about 10 g, more preferably about 3 g to about 7 g of HMOs.

Preferably, the one or more HMOs are administered to a human, preferably a non-infant human, in need in two steps:
(a) in a first step, during an initial treatment period of about 14 days, to increase the relative abundance of bifidobacteria of the phylogenetic *Bifidobacterium adolescentis* group; and
(b) in a second step, during an additional period of treatment of 1 or more days following the initial treatment period, to increase the relative abundance of *Bifidobacterium longum* and/or *Bifidobacterium bifidum*, in the microbiota in the gastro-intestinal tract of said human.

DETAILED DESCRIPTION OF THE INVENTION

It has now been surprisingly found that administration of human milk oligosaccharides (HMOs) to humans, in particular non-infant humans, preferentially increases the abundance of bifidobacteria in the gastrointestinal tract and improves gut motility. The increase of bifidobacteria could lead to regulation of serotonin synthesis, and hence affect gut motility and secretion. Since species of bifidobacteria are able to synthesize tryptophan, and in addition, can inhibit production of pro-inflammatory cytokines such as TNF-$\alpha$ and IFN-$\gamma$, selective stimulation of these bacteria can affect tryptophan metabolism shunting it down the serotonin pathway instead of the kynurenine pathway causing improvement of gut motility and secretion. Furthermore, fucosylated HMOs can directly regulate gut motor contraction.

Thus, it has been discovered that HMOs can, by oral or enteral ingestion, modulate the intestinal microbiota in humans, in particular non-infant humans, by preferentially promoting the growth of bifidobacteria. As an outcome, the synthesis of serotonin is up-regulated and improvement of gut motility and secretion is obtained.

Terms and Definitions

The term "human milk oligosaccharide" or "HMO" preferably means a complex carbohydrate found in human breast milk that can be in acidic or neutral form. More than about 200 different HMO structures are known to exist in human breast milk (Urashima et al.: Milk Oligosaccharides, Nova Biomedical Books, New York, 2011). HMOs can be backbone, fucosylated and sialylated oligosaccharides. Backbone HMOs consists of Glu, Gal and GlcNAc and are devoid of Fuc and sialic acid. Examples of backbone HMOs include lacto-N-tetraose (LNT), lacto-N-neotetraose (LNnT), lacto-N-neohexaose (LNnH) and lacto-N-hexaose (LNH). Fucosyl HMOs are fucosylated lactoses or fucosylated backbone HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose 1 (FLNH-I), fucosyl-lacto-N-hexaose III (FLNH-III) and fucosyl-para-lacto-N-neohexaose (F-pLNnH). Sialyl HMOs are sialylated lactoses or sialylated backbone HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyllacto-N-tetraose (LST b). HMOs containing both sialyl and fucosyl groups may be considered to belong to either of the latter two groups. Examples for sialyl and fucosyl HMOs include disialyl-fucosyl-lacto-N-hexaose II (DSFLNH-II), fucosyl-sialyl-lacto-N-neohexaose 1 (FSLNnH-1), fucosyl-sialyl-lacto-N-hexaose 1 (FSLNH-I) and 3-fucosyl-3'-sialyllactose (FSL). In context of the present invention, lactose is not included in the group of HMOs.

The terms "microbiota", "microflora" and "microbiome" preferably mean a community of living microorganisms that typically inhabits a bodily organ or part. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level the microorganisms of *Bacteroides, Faecalibacterium, Bifidobacterium, Roseburia, Alistipes, Collinsella, Blautia, Coprococcus, Ruminococcus, Eubacterium* and *Dorea*; and at species level microorganisms of *Bacteroides uniform is, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. In some instances, the gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The term "bifidobacteria" means a member of the *Bifidobacterium* genus commonly found in the human gastrointestinal tract. Examples of bifidobacteria are *Bifidobacterium longum, Bifidobacterium bifidum*, and the members of the phylogenetic *Bifidobacterium adolescentis* group. In non-infant humans, bifidobacteria preferably include members of *Bifidobacterium longum, Bifidobacterium bifidum*, and the phylogenetic *Bifidobacterium adolescentis* group, for example *Bifidobacterium pseudocatenulatum* and/or *Bifidobacterium adolescentis*.

The term "serotonin" refers to the compound having the IUPAC name 3-(2-aminoethyl)-5-hydroxyindole, and the following structural formula:

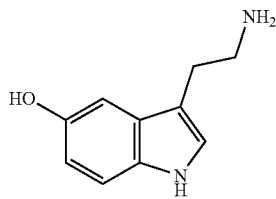 [SMILES: NCCc1c[nH]c2ccc(O)cc12]

Serotonin is also known as 5-hydroxytryptamine, enteramine, thrombocytin, 3-(3-aminoethyl)-5-hydroxyindole, thrombotonin and 5-HT.

The term "serotonin dysregulation" means that the level of serotonin in blood of a human subject deviates from the level which is typically regarded to be normal, i.e. it is lower or higher than 101-283 ng/ml.

The term "tryptophan" refers to the amino acid having the IUPAC name (2S)-2-amino-3-(1H-indol-3-yl) propanoic acid, and the following structural formula:

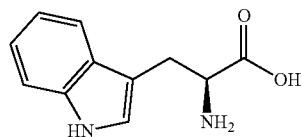 [SMILES: N[C@@H](Cc1c[nH]c2ccccc12)C(=O)O]

The term "tryptophan dysregulation" means that the level of tryptophan in blood of a human subject deviates from the level which is typically regarded to be normal, i.e. it is lower or higher than 25-73 μmol/l.

The term "symptom or disease associated with serotonin and/or tryptophan dysregulation" refers to a symptom or disease preferably selected from the following group: depression, anxiety, anger, being unusually sensitive to pain, carbohydrate cravings and binge eating, constipation, digestive disorders, feeling glum from lack of sunlight, feeling overly dependent on others, feeling overwhelmed, hypervigilance, insomnia, joylessness, low self-esteem, migraines, poor cognitive function and tinnitus.

The term "synthetic composition" designates a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition of the invention typically comprises one or more compounds, advantageously HMOs, that are capable of preferentially increasing the abundance of bifidobacteria, in particular *Bifidobacterium* of the following species: *Bifidobacterium longum, Bifidobacterium bifidum*, and/or members of the phylogenetic *Bifidobacterium adolescentis* group. In some embodiments, the synthetic composition may comprise one or more compounds or components other than HMOs that may have an effect on bifidobacteria of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

The term "relative abundance of bifidobacteria", preferably, means the abundance of bifidobacteria relative to other genus in the microbiota of the gastro-intestinal tract.

The term "relative growth of bifidobacteria", preferably, means the growth of bifidobacteria relative to other genus in the microbiota in the gastro-intestinal tract.

The term "human" preferably means a non-infant human individual. The term "non-infant human" or "non-infant" means in the present context a human of 3 years of age and older. A non-infant human can be a child, a teenager, an adult or an elderly.

The term "enteral administration" preferably means any conventional form for delivery of a composition to a human that causes the deposition of the composition in the gastro-intestinal tract (including the stomach). Methods of enteral administration include feeding through a naso-gastric tube or jejunum tube, oral, sublingual and rectal.

The term "oral administration" preferably means any conventional form for the delivery of a composition to a human through the mouth thereby depositing the composition in the gastrointestinal tract (including the stomach) of the patient. Accordingly, oral administration includes swallowing of composition by the patient, enteral feeding through a naso-gastric tube, and the like. Oral administration is a form of enteral administration.

The term "effective amount" preferably means an amount of a composition that provides an HMO in a sufficient amount to render a desired treatment outcome in a human. An effective amount can be administered in one or more doses to achieve the desired treatment outcome.

The term "irritable bowel syndrome" (also abbreviated herein as IBS) means a clinically heterogeneous disorder of human, particularly adult human individuals, wherein the patients have chronic symptoms such as abdominal pain, abdominal discomfort, abdominal bloating, fatigue, and changes in bowel movement patterns, such as patterns of loose or more frequent bowel movements, diarrhoea and constipation. Routine clinical tests on IBS patients typically show no abnormalities, although their bowels may be more sensitive to certain stimuli, such as balloon insufflation testing. Individuals having the later and other symptoms (than listed above) are also contemplated as subjects of the present invention. There are at least three forms of IBS, depending on which symptom predominates: (1) diarrhoea-predominant (IBS-D); (2) constipation-predominant (IBS-C); and (3) IBS with alternating stool pattern (IBS-A or IBS-M). There are also various clinical subtypes of IBS, such as post-infectious IBS (IBS-PI) or unsubtyped IBS (IBS-U).

The term "prophylaxis" refers to a measure taken to maintain health and prevent occurrence of undesirable physiological or psychological conditions or spread of symptoms of a disease.

The term "treatment" refers to an attempt to remediate a health problem, e.g. a physiological or psychological condition or symptom of a disease, usually following a diagnosis.

The term "initial period" of treatment with an HMO or an HMO mixture is about 14 days from the start of the treatment; "additional period" of treatment means 1 or more days following the initial period of treatment.

The term "about" in the present context means up to 2.5% deviation from the corresponded value.

The term "preferably" is used herein to indicate the best mode of invention that does not limit the scope of invention.

Embodiments of the Invention

HMOs for use in
the prophylaxis or treatment of a symptom or disease associated with serotonin and/or tryptophan dysregulation in a human,
the prophylaxis or treatment of serotonin and/or tryptophan dysregulation in a human, in particular in an irritable bowel symptom (IBS) patient, or
improving physiological and/or psychological conditions associated with serotonin and/or tryptophan dysregulation in a human,
may be a single HMO, or a mixture of any HMOs suitable for the purposes of the invention. Preferably, the HMO is a fucosylated or a non-fucosylated neutral HMO. More preferably, the HMOs for prophylaxis or treatment of non-infectious diarrhoea in a human is a mixture of at least a first HMO and at least a second HMO, where the first HMO is a fucosylated neutral HMO and the second HMO is a non-fucosylated neutral HMO. Particularly, the mixture contains a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture contains a fucosylated HMO selected from the list consisting of 2'-FL, 3-FL and DFL, and a non-fucosylated HMO selected from the list consisting of LNT and LNnT; advantageously the mixture comprises 2'-FL and/or DFL and LNnT and/or LNT. In some embodiments, the mixture essentially consists of two neutral HMOs, e.g. a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture essentially consists of a fucosylated HMO selected from the list consisting of 2'-FL, 3-FL and DFL, and a non-fucosylated HMO selected from the list consisting of LNT and LNnT; in one preferred embodiment the mixture essentially consists of 2'-FL and LNnT, in another preferred embodiment the mixture essentially consists of 2'-FL and LNT. The mixture may also contain sialylated HMOs such as 3'-SL and 6'-SL.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The synthetic composition for use in
the prophylaxis or treatment of a symptom or disease associated with serotonin and/or tryptophan dysregulation in a human,
the prophylaxis or treatment of serotonin and/or tryptophan dysregulation in a human, in particular in an irritable bowel symptom (IBS) patient, or
improving physiological and/or psychological conditions associated with serotonin and/or tryptophan dysregulation in a human,
may comprise a single HMO or a mixture of any HMOs suitable for the purpose of the invention. The HMOs may be selected as described above.

A synthetic composition of this invention comprising one or more human milk oligosaccharides, can take any suitable form. For example, the composition can be in the form of a nutritional composition which contains other macronutrients such as proteins, lipids or other carbohydrates, preferably where the other carbohydrate is lactose and/or a carbohydrate different than an HMO. The synthetic composition can also be a pharmaceutical composition.

In one embodiment, the synthetic composition may be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to humans. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antiviral agents, antibiotics, probiotics, analgesics, and anti-inflammatory agents. The proper dosage of these compositions for a human can be determined in a conventional manner, based upon factors such as severity of the lactose intolerance, immune status, body weight and age. The required amount would generally be in the range from about 200 mg to about 20 g per day, in certain embodiments from about 1 g to about 15 g per day, from about 3 g to about 10 g per day, in certain embodiments from about 3 g to about 7 g per day. Appropriate dose regimes can be determined by conventional methods.

In another embodiment, the synthetic composition may be a nutritional composition. The nutritional composition can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Preferably the protein source contains no or low concentrations of lactose. The protein can also be provided in the form of free amino acids. The protein can comprise about 5% to about 30% of the energy of the nutritional composition, normally about 10% to 20%.

The protein source can be a source of glutamine, threonine, cysteine, serine, proline, tryptophan or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can reduce permeability. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, glucose, fructose, maltose, trehalose, sucrose, honey, sugar alcohols (e.g., maltitol, erythritol, sorbitol), or mixtures thereof. Preferably the carbohydrate source is free from lactose. Generally, digestible carbohydrates may provide about 35% to about 55% of the energy of the nutritional composition. A particularly suitable digestible carbohydrate is a low dextrose equivalent (DE) maltodextrin. In some embodiments, the composition may also comprise indigestible saccharides, such as e.g. lactulose.

Suitable lipids may include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for non-infants with inflamed GI tracts. Generally, the lipids may provide about 35% to about 50% of the energy of the nutritional composition. The lipids can contain essential fatty acids (omega-3 and omega-6 fatty acids). Preferably, these polyunsaturated fatty acids provide less than about 30% of total energy of the lipid source. Decreasing the levels of these polyunsaturated fatty acids is believed to decrease sensitivity to peroxidation; which can be beneficial for non-infants having inflammatory conditions.

Suitable sources of long chain triglycerides may be selected from rapeseed oil, sunflower seed oil, palm oil, soy oil, milk fat, corn oil, high oleic oils, and soy lecithin. Fractionated coconut oils can be a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition can also include vitamins and minerals. If the nutritional composition is intended to be a sole source of nutrition, it preferably includes a complete vitamin and mineral profile. Examples of vitamins include, but not limited to, vitamins A, B-complex (such as B1, B2, B6 and B12), C, D, E and K, niacin and acid vitamins such as pantothenic acid, folic acid and biotin. Examples of minerals include, but not limited to, calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition can also contain various other conventional ingredients such as preservatives, emulsifying agents, thickening agents, buffers, fibres and probiotics, especially probiotics which can help to reduce symptoms in IBS patients (e.g. VSL #3, *B. infantis* 35624, *B. animalis* subsp. *lactis* BB-12, *B. lactis* Bi-07, *L. rhamnosus* GG, *L. rhamnosus* Lc705, *L. plantarum* DSM 9843, *L. plantarum* CECT7484, *L. plantarum* CECT7485, *L. acidophilus* NCFM, *L. fermentum* CECT5716, *B. breve* Bb99, *Propionibacterium* freundenreichii ssp. *Shermanii* JS, *P. acidilactici* CECET7483, *Streptococcus faecium*), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. The composition can be fed to a human via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, the total concentration of HMOs in the liquid, by weight of the liquid, is from about 0.02% to about 2.0%, including from about 0.1% to about 1.5%, including from about 0.3% to about 1.0%. When the nutritional product is a concentrated nutritional liquid, the total concentration of HMOs in the liquid, by weight of the liquid, is from about 0.04% to about 4.0%, including from about 0.2% to about 3.0%, including from about 0.6% to about 2.0%.

The synthetic composition can also be in a unit dosage form such as a capsule, tablet or sachet. For example, the synthetic composition can be in a tablet form comprising the HMOs, and one or more additional components to aid formulation and administration, such as diluents, excipients, antioxidants, lubricants, colorants, binders, disintegrants, and the like.

Suitable diluents, excipients, lubricants, colorants, binders, and disintegrants include, but not limited to, polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQ10") and glutathione.

The unit dosage forms, especially those in sachet form, can also include various nutrients including macronutrients.

The unit dosage forms can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The unit dosage forms can also be administered by rectal suppository, aerosol tube, naso-gastric tube or direct infusion into the GI tract or stomach.

The unit dosage forms can also include therapeutic agents such as antiviral agents, antibiotics, probiotics, analgesics, and anti-inflammatory agents. The synthetic composition in unit dosage form may be a pharmaceutical composition or a nutritional supplement.

For reducing or preventing serotonin and/or tryptophan dysregulation, as well as a disease or symptoms associated with serotonin and/or tryptophan dysregulation in a patient, the amount of HMO(s) required to be administered to the patient will vary depending upon factors such as the risk and severity of the disease, the age of the patient, the form of the composition, and other medications being administered to the patient. However, the required amount can be readily set by a medical practitioner and would generally be in the range from about 200 mg to about 20 g per day, in certain embodiments from about 1 g to about 15 g per day, from about 3 g to about 10 g per day, in certain embodiments from about 3 g to about 7.5 g per day. An appropriate dose can be determined based on several factors, including, for example, body weight and/or condition, the severity of the condition, being treated or prevented, other ailments and/or diseases, the incidence and/or severity of side effects and the manner of administration. Appropriate dose ranges may be determined by methods known to those skilled in the art. During an initial treatment phase, the dosing can be higher or lower depending upon the need to boost bifidobacteria abundance or initial tolerance to HMOs. During a maintenance phase, the dosing can be set for chronic long term use.

The duration of the HMO administration will vary depending upon factors such as the risk and severity of the medical condition, age, the form of the composition, the dose and other medications being administered. However, the duration can be readily set by a medical practitioner. For example, the duration may be for 1 to 3 months. The administration can continue chronically for an indefinite period.

Whilst the invention has been described with reference to a preferred embodiment, it will be appreciated that various modifications are possible within the scope of the invention.

EXAMPLE

The following working example is described to illustrate the invention and should not be considered as limiting the scope of invention.

Example 1—Human Trial

A total of 60 male and female IBS patients are recruited to participate in the study. After a screening visit and run-in period of 1-2 weeks, the patients are selected. The patients are randomized into three groups, each of 20 patients, with two groups consuming the treatment product and one group the placebo product for 4 weeks. The treatment product contains either 5 or 10 grams of a combination of 2'-FL and LNnT in a 4:1 ratio, while the placebo product contains 5 grams glucose. Both products are in powder form in a unit dosage container.

The patients are eligible to participate if they are at an age between 18-60 years, fulfil definition of IBS-D, IBS-C or IBS-A/M according to the Rome IV criteria for IBS and have a global IBS-SSS score of >174 during the 2 weeks run-in period. All recruited patients are able and willing to understand and comply with the study procedures. Patients are excluded if: they have any known gastrointestinal disease(s) that may cause symptoms or interfere with the trial outcome, in particular lactose intolerance and coeliac disease; they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 1 months prior to the study; consumed antibiotic drugs 1 months prior to the study; consumed on a regular basis any medication that might interfere with symptom evaluation 2 weeks prior to the study; diagnosed with and treated for IBS for more than 10 years; and pregnant or lactating.

At the screening visit, clinical and medical history and concomitant medication is registered. IBS diagnostic criteria will be assessed and part 2 of the IBS-SSS questionnaire will be completed.

A faecal sample kit is distributed together with the Bristol Stool Form Scale (BSFS) and Bowel Movement Diary (BMD) to be filled in during the 7 days just prior to visit 2. Patients will be asked to register their diet 3 days just prior to visit 2, and will be reminded not to change their usual diet during the study.

At the second visit, eligibility criteria are checked and eligible subjects are randomised to the three arms in the trial. A physical examination is done and a number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Based on clinical symptoms and data from questionnaires, patients are characterised into one of the three following groups; diarrhoea predominant (IBS-D), constipation predominant (IBS-C) or alternating/mixed (IBS-A/M). This enables allocation of patients from each subgroup into the intervention groups. When allocated to the groups patients are provided with either treatment or placebo products. Sigmoidoscopy is performed and mucosal biopsies and faecal aspirates taken. Patients are asked about any adverse events and any changes in their usual medication. The BSFS and BMD is collected and new forms, to be filled in daily during the intervention period, are distributed. Faecal samples are collected and equipment for new samples are distributed. Blood samples are collected for routine clinical chemistry and haematology and biomarker analysis and a saliva sample is collected to analyse FUT2 secretor status. Diet records are collected, and patients are asked to register their diet for 3 days just prior to visit 3. Patients are reminded not to change their usual diet during the study.

At the third visit, a physical examination is performed and a number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Remaining study products and compliance diaries are collected to check compliance. Blood samples are collected for routine clinical chemistry and haematology and biomarker analysis, and sigmoidoscopy is performed and mucosal biopsies and faecal aspirates taken. Patients are asked about any adverse events and any changes in their usual medication. Faecal samples are collected and equipment for collecting new samples distributed. The BSFS and BMD is collected and new forms, to be filled in during the 7 days just prior to visit 4, are distributed. Diet records are collected, and patients are reminded not to change their usual diet during the study.

The treatment period lasts 4 weeks, the patients are administered 5 or 10 g of mix of 2'-FL+LNnT or 5 g of glucose daily. Patients are instructed to consume the products in the morning with breakfast. Compliance is monitored through the interactive internet enabled system.

At the end of the study, each patient has an exit visit with the medical team. Faecal samples and blood samples are collected and analysed as before. A number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Patients are asked about any adverse events and any changes in their usual medication or diet, and the BSFS and BMD is collected.

To assess the microbiota profile, DNA is extracted from faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. *Nucleic Acids Res.* 41, e1 (2013)). These are universal bacterial 16S rDNA primers, which target the V3-V4 region. Following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH is used for bioinformatical analysis of the sequence data.

Plasma tryptophan and serotonin are determined using High Performance Liquid Chromatography (HPLC). The mobile phase consisted of 50 mmol/l acetic acid, 100 mmol/l Zinc Acetate with 3% (v/v) acetonitrile is filtered through a 0.45 lm Millipore filter (AGB, Dublin, Ireland) and vacuum degassed prior to use. Separations are achieved by isocratic elution at 0.3 mL/min. The fluorescent detector is set to an excitation wavelength of 254 nm and an emission wavelength of 404 nm. The PDA detector start wavelength is 210 nm and the end wavelength is 400 nm with chromatogram extraction at 330 nm. Working standard dilutions are prepared from millimolar stock solutions of each standard and stored at −80° C. until required for analysis. Plasma samples are deproteinized by the addition of 20 µl of 4 mol/l perchloric acid to 200 µl of plasma spiked with 3-nitro-L-tyrosine as internal standard. Twenty microlitres of either sample or standard is injected onto the HPLC system and chromatograms generated are processed using Waters Empower software.

Biopsies are fixed and stained with haematoxylin eosin and immunostained by use of the avidin biotin complex (ABC) method using the Vectastain ABC kit (Vector Laboratories). The antibody used for immunostaining for serotonin is monoclonal mouse anti-serotonin (DakoCytomation, code no. 5HT-209).

Measurement of plasma IFN-γ and TNF-α was performed using an electro-chemiluminescence multiplex system Sector 2400 imager from Meso Scale Discovery (Gaithersburg, Md., USA) where antibodies labelled with Sulfo-tag reagents emitted light upon electrochemical stimulation.

The results show that oral ingestion of HMOs modulate the intestinal microbiota, and specifically stimulate the abundance of bifidobacteria. The abundance of bifidobacteria resulted in an increase in plasma tryptophan. Additionally, serotonin level both in plasma and the biopsies correlated positively with the tryptophan level, and negatively with the IFN-γ and TNF-α concentration in the IBS patients given HMOs. Interestingly, the results show that supplementing with HMOs affected gut motility shown by decrease in stool frequency and improvement of consistency in the IBS-D patients; and increase in stool frequency and softening stool consistency in IBS-C patients; and normalisation of frequency and consistency in IBS-A patients. Collectively, HMOs are able to increase bifidobacteria and tryptophan levels, and hereby affect the regulation of the serotonin pathway which contribute to improvement in gut motility in IBS patients.

The invention claimed is:

1. A method of increasing the relative abundance of *Bifidobacterium adolescentis* in the gastrointestinal tract and regulating levels of one or both of tryptophan and serotonin in a non-infant human, the method comprising:
    administering for an initial treatment period an amount of a mixture of human milk oligosaccharides (HMOs) comprising one or more fucosylated HMOs selected from 2'-FL, 3-FL, LNFP-I and DFL, and one or more non-fucosylated HMOs selected from LNT and LNnT, wherein the amount is effective to increase the relative abundance of *Bifidobacterium adolescentis* in the gastrointestinal tract of the non-infant human.

2. The method of claim 1, wherein the non-infant human is an irritable bowel syndrome (IBS) patient.

3. The method of claim 1, wherein during the initial treatment period the selected amount of the mixture of HMOs that is effective to increase the relative abundance of *Bifidobacterium adolescentis* in the gastrointestinal tract of the non-infant human is from 3 g to 10 g per day.

4. The method of claim 1, wherein the selected amount of the mixture of HMOs is effective to increase the level of serotonin in the blood of the non-infant human.

5. The method of claim 1, wherein administering to the non-infant human the selected amount of the mixture of HMOs further comprises:
    administering, during a maintenance treatment period of one or more days following the initial treatment period, a reduced amount, relative to the selected amount administered during the initial treatment period, of the mixture of HMOs that is effective for increasing the relative abundance of one or both of *Bifidobacterium longum* and *Bifidobacterium bifidum* in the microbiota in the gastrointestinal tract of the non-infant human.

6. The method of claim 1, wherein the selected amount of the mixture of HMOs is effective to decrease the concentration of one or both of IFN-γ and TNF-α in the blood of the non-infant human.

7. The method of claim 1, wherein the one or more fucosylated HMOs are selected from 2'-FL, LNFP-I, and DFL, and the one or more fucosylated HMOs are present in a mass ratio relative to the one or more non-fucosylated HMOs of from about 5:1 to 1:1.

8. The method of claim 1, wherein the mixture of HMOs consists essentially of one or more fucosylated HMOs selected from 2'-FL, 3-FL and DFL, and one or more non-fucosylated HMOs selected from LNT and LNnT.

9. The method of claim 5, wherein the maintenance treatment period is at least one month.

10. A method of increasing the relative abundance of *Bifidobacterium adolescentis* and regulating serotonin to improve gut motility in a non-infant human with irritable bowel syndrome (IBS), the method comprising:
    selecting an amount of a mixture of 2'-FL and LNnT, the amount effective to increase the relative abundance of *Bifidobacterium adolescentis* in the gastrointestinal tract of the non-infant human; and
    increasing the relative abundance of *Bifidobacterium adolescentis* in the gastrointestinal tract of the non-infant human and regulating serotonin to improve gut motility by administering to the non-infant human the selected amount of the mixture.

11. The method of claim 10, wherein the non-infant human is an IBS-D patient and the method further comprises decreasing stool frequency and improving stool consistency by administering to the non-infant human the selected amount of the mixture.

12. The method of claim 10, wherein the non-infant human is an IBS-C patient and the method further comprises increasing stool frequency and softening stool consistency by administering to the non-infant human the selected amount of the mixture.

13. The method of claim 10, wherein the non-infant human is an IBS-A patient and the method further comprises normalizing stool frequency and stool consistency by administering to the non-infant human the selected amount of the mixture.

* * * * *